United States Patent
Kouwen et al.

(10) Patent No.: US 11,674,117 B2
(45) Date of Patent: Jun. 13, 2023

(54) STREPTOCOCCUS THERMOPHILUS STARTER CULTURES

(71) Applicant: DSM IP Assets B.V., Heerlen (NL)

(72) Inventors: Roelof Hendrik Matthijs Kouwen, Echt (NL); Douwe Van Sinderen, D. Cork (IE); Brian McDonnell, Cork (IE); Pieter Emiel Verloren Van Themaat, Echt (NL); Jennifer Mahony, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 999 days.

(21) Appl. No.: 16/470,856

(22) PCT Filed: Dec. 14, 2017

(86) PCT No.: PCT/EP2017/082776
§ 371 (c)(1),
(2) Date: Jun. 18, 2019

(87) PCT Pub. No.: WO2018/114573
PCT Pub. Date: Jun. 28, 2018

(65) Prior Publication Data
US 2019/0367866 A1    Dec. 5, 2019

(30) Foreign Application Priority Data
Dec. 20, 2016   (EP) .................... 16205245

(51) Int. Cl.
*C12N 1/20* (2006.01)
*A23C 9/123* (2006.01)
*C12Q 1/689* (2018.01)
*C12R 1/46* (2006.01)
*G16B 35/20* (2019.01)

(52) U.S. Cl.
CPC .............. *C12N 1/20* (2013.01); *A23C 9/1238* (2013.01); *C12N 1/205* (2021.05); *C12Q 1/689* (2013.01); *G16B 35/20* (2019.02); *A23Y 2240/75* (2013.01); *C12R 2001/46* (2021.05)

(58) Field of Classification Search
CPC ........ C12N 1/20; C12N 1/205; A23C 9/1238; G16B 35/20; A23Y 2240/75; C12R 2001/46; C12Q 1/689
See application file for complete search history.

(56) References Cited

FOREIGN PATENT DOCUMENTS

WO    2008040734 A1    4/2008

OTHER PUBLICATIONS

Palindungan et al., Microbial Genomics, 2022; 8:000803, p. 1-14.*
Romero et al., FEMS Microbiology Reviews, fuaa048, 2020, p. 909-932.*
Quiberoni, A. et al., "Characterization of phage receptors in *Streptococcus thermophilus* using purified cell walls obtained by a simple protocol", Journal of Applied Microbiology, 2000, pp. 1059-1065, vol. 89.
Hols, Pascale, et al., "New insights in the molecular biology and physiology of *Streptococcus thermophilus* revealed by comparative genomics," FEMS Microbiology Reviews, (2005), vol. 29: 435-463.
Goh, Yong, et al., "Specialized adaptation of a lactic acid bacterium to the milk environment: the comparative genomics of *Streptococcus thermophilus* LMD-9," Microbial Cell Factories, (2011), vol. 10: S22: 1-17.

* cited by examiner

*Primary Examiner* — Kade Ariani
(74) *Attorney, Agent, or Firm* — McBee Moore & Vanik IP, LLC (57) ABSTRACT

The present invention relates to a starter culture comprising at least two *Streptococcus thermophilus* strains, wherein a first and a second *Streptococcus thermophilus* strain are chosen from RGP group 1, RGP group 2, RGP group 3 and RGP group 4, with the proviso that the first and second *Streptococcus thermophilus* strains do not belong to the same RGP group.

12 Claims, 5 Drawing Sheets
Specification includes a Sequence Listing.

| Phages | ST13 | ST4576 | ST4577 | ST800 | UCCST4 | ST820 | UCCST5 | UCCST11 | ST665 | 300-F | ST3 | UCCST7 | ST14 | ST802 | ST144 | 100-F | NGB48.1 | UCCST6 | ST110 | UCCT1 | 200-E |
|---|---|---|---|---|---|---|---|---|---|---|---|---|---|---|---|---|---|---|---|---|---|
|  | RGP group 1 | | | | | | | | RGP group 2 | | | | | RGP group 3 | | RGP group 4 | | | | | |
| ST13D1A-L | + | + | + |  |  |  | + | + |  |  |  |  |  |  |  |  |  |  |  |  |  |
| ST13D2A-L | + | + | + |  |  |  | + |  |  |  |  |  |  |  |  |  |  |  |  |  |  |
| ST13D4A-L | + | + | + |  |  |  | + |  |  |  |  |  |  |  |  |  |  |  |  |  |  |
| ST4576D1A-L | + | + | + |  |  |  | + |  |  |  |  |  |  |  |  |  |  |  |  |  |  |
| ST4576D2A-L | + | + | + |  |  |  | + |  |  |  |  |  |  |  |  |  |  |  |  |  |  |
| ST4577D1A-L | + | + | + |  |  |  | + | + |  |  |  |  |  |  |  |  |  |  |  |  |  |
| ST4577D3A-L | + | + | 1 |  |  |  | 1 | + |  |  |  |  |  |  |  |  | 1 | 1 |  |  |  |
| ST800D1B-L | + |  |  | + |  |  | + |  |  |  |  |  |  |  |  |  |  |  |  |  |  |
| ST4A3 |  |  |  |  | + | + |  |  |  |  |  |  |  |  |  |  |  |  |  |  |  |
| ST5B1 | + | + | + |  |  |  | + |  |  |  |  |  |  |  |  |  |  |  |  |  |  |
| ST11F | 1 |  | 1 | + |  |  | 1 | + |  |  |  |  |  |  |  |  |  |  |  |  |  |
| ST7B3 |  |  |  | 1 |  |  | 1 | 1 |  |  |  | + | + |  |  |  |  |  |  |  |  |
| ST665D2A-S |  |  |  | 1 |  |  |  |  | + |  |  | + |  |  |  |  |  |  |  |  |  |
| 300FD2A-L |  |  |  | 1 |  |  |  |  |  | + | + |  | + |  |  |  |  |  | 1 |  |  |
| W1A |  |  |  | 1 |  |  |  |  |  |  | 1 | 1 | + | + |  |  |  |  |  |  |  |
| W3B |  |  |  |  |  |  |  |  |  |  | 1 | 1 | + | + |  |  |  |  |  |  |  |
| ST802D1B-E | 1 |  |  |  |  |  |  |  |  |  |  |  |  | + |  |  |  |  |  |  |  |
| ST144D1A-M |  |  |  |  |  |  |  |  |  |  |  |  |  | + | 1 |  |  |  |  |  |  |
| NGBD1A-L |  |  |  |  |  |  |  |  |  |  |  |  |  |  |  | + | + |  | + |  |  |
| ST6B2 |  |  |  |  |  |  |  |  |  |  |  |  |  |  |  |  |  | + | + |  |  |
| W3A |  |  |  |  |  |  |  |  |  |  |  |  |  |  |  |  |  | + | + |  |  |
| W7D | 1 |  |  |  | 1 |  |  |  |  |  |  |  |  |  |  |  |  | + | + |  |  |
| T1A |  |  |  |  |  |  |  |  |  |  |  |  |  |  |  |  |  |  | + | + | + |
| ST110D1A-L |  |  |  |  |  |  |  |  |  |  |  |  |  |  |  |  |  | + | + |  |  |

Fig. 4

Fig. 5 ized entry of International Application No. PCT/EP2017/082776, filed 14 Dec. 2017, which claims priority to European Patent Application No. 16205245.0, filed 20 Dec. 2016.

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: RGP group1 forward primer

<400> SEQUENCE: 1
ggatgatggt tcgacggata g                                       21
```

<210> SEQ ID NO 2
<211> LENGTH: 20
<212> TYPE: DNA
<213> ORGANISM: Artificial Sequence
<220> FEATURE:
<223> OTHER INFORMATION: RGP group1 reverse primer

<400> SEQUENCE: 2
ccgctcttcc aaaaccatga				20

<210> SEQ ID NO 3
<211> LENGTH: 631
<212> TYPE: DNA
<213> ORGANISM: Streptococcus thermophilus
<220> FEATURE:
<221> NAME/KEY: misc_feature
<223> OTHER INFORMATION: RGP group1 amplicon

<400> SEQUENCE: 3
ggatgatggt tcgacggata gttcaactca aattatccaa gaggttttga aggattcacc		60 ttttgagaca agatttgaaa ctcatgaaaa ccttggggta gtaaagaatc gaaatttagg		120 attagagctt ataagaggtg actatttgct atttgtagat agtgataact acctcgatgc		180 ggattatgtg gaacagttgt acagtaagtt gacggaaaca aatgctgata ttgcgtactg		240 tgatcttttt aatccagaaa aagaagagtt ctaccttaaa agccgtgaat ttgacctaac		300 tgccttttcta aatgctagtt ttattgataa ctgttctttg attcgtagaa gtattattgg		360 aaatgctcgt tatgatgaga tgttaaatcg taaaaagctt gaagattatg acttttatt		420 gaacttaatc attaataacg gtgctaaagc ggtatatcaa ccaagcacta agcttaatta		480 tcgtgtcttt gaaacaggat caatttctgg acgtgactcc gttcgctacc attatgaaat		540 ctatcttgac attcttgaga agtaccttga taagcttcct catgaaattt acaaggcagt		600 ttgtgagaac ctcatggttt tggaagagcg g				631

<210> SEQ ID NO 4
<211> LENGTH: 21
<212> TYPE: DNA
<213> ORGANISM: Artificial Sequence
<220> FEATURE:
<223> OTHER INFORMATION: RGP group2 forward primer

<400> SEQUENCE: 4
gtgaagagtc agaagacgaa t				21

<210> SEQ ID NO 5
<211> LENGTH: 19
<212> TYPE: DNA
<213> ORGANISM: Artificial Sequence
<220> FEATURE:
<223> OTHER INFORMATION: RGP group2 reverse primer

<400> SEQUENCE: 5
caaaggcccc gatggtatt				19

<210> SEQ ID NO 6
<211> LENGTH: 464
<212> TYPE: DNA
<213> ORGANISM: Streptococcus thermophilus
<220> FEATURE:
<221> NAME/KEY: misc_feature
<223> OTHER INFORMATION: RGP group2 amplicon

<400> SEQUENCE: 6

```
gtgaagagtc agaagacgaa taattgattt gttttatat tcatagcaat ggcgacttga      60
acagtcgctt ttcttttgt attaggaaaa aagcccagaa aatggtataa ttgagtggat    120
tgtaatttgt aagaaaggaa ataatatgca acacgttttt attatcggaa gtcgtggact    180
tccggctcaa tatggtggtt tcgagacctt cgtggaccaa ttggtctcca atcgagtatc    240
accgaatatc aagtaccatg ttgcttgcct ttctaatgat caagcctact atcattttga    300
ctacaagggt gtagattgtt ttacgattaa agcacccaaa cttgggcctg cgcgggtcat    360
tgcctatgat atgatggcca tcaattatgc cttgaaggtc attaagaaac aaggaattga    420
aaaacctatt tttatatttt tgggcaatac catcggggcc tttg                    464
```

<210> SEQ ID NO 7
<211> LENGTH: 21
<212> TYPE: DNA
<213> ORGANISM: Artificial Sequence
<220> FEATURE:
<223> OTHER INFORMATION: RGP group3 forward primer

<400> SEQUENCE: 7

```
gaggaagcaa cagataaacg a                                              21
```

<210> SEQ ID NO 8
<211> LENGTH: 21
<212> TYPE: DNA
<213> ORGANISM: Artificial Sequence
<220> FEATURE:
<223> OTHER INFORMATION: RGP group3 reverse primer

<400> SEQUENCE: 8

```
gaccaattgg tccacaaaag t                                              21
```

<210> SEQ ID NO 9
<211> LENGTH: 303
<212> TYPE: DNA
<213> ORGANISM: Streptococcus thermophilus
<220> FEATURE:
<221> NAME/KEY: misc_feature
<223> OTHER INFORMATION: RGP group3 amplicon

<400> SEQUENCE: 9

```
gaggaagcaa cagataaacg agaatatttt gtttatgtta ttgccaatct atttatattg     60
atgtcagtag tattgacaat ccttcagtac tatggtgtga aaataatttt ttaactttt    120 tcaagtagtc ctttgtggct gcttttctgt ttgcaatagg caaatctttt gtaaatggt    180 ataattgact agattataga cttgttagaa aggggattta tgcaacaaca cgtattcatt    240
attggaagtc gtgggcttcc gtctcaatat ggcggttttg agacttttgt ggaccaattg    300
gtc                                                                 303
```

<210> SEQ ID NO 10
<211> LENGTH: 18
<212> TYPE: DNA
<213> ORGANISM: Artificial Sequence
<220> FEATURE:
<223> OTHER INFORMATION: RGP group4 forward primer

<400> SEQUENCE: 10

```
ctcctcgtac tcacccac                                                  18
```

<210> SEQ ID NO 11
<211> LENGTH: 21

```
<212> TYPE: DNA
<213> ORGANISM: Artificial Sequence
<220> FEATURE:
<223> OTHER INFORMATION: RGP group4 reverse primer

<400> SEQUENCE: 11
gcacaagata cagctcgtta c                                              21

<210> SEQ ID NO 12
<211> LENGTH: 162
<212> TYPE: DNA
<213> ORGANISM: Streptococcus thermophilus
<220> FEATURE:
<221> NAME/KEY: misc_feature
<223> OTHER INFORMATION: RGP group4 amplicon

<400> SEQUENCE: 12
ctcctcgtac tcacccacaa ttttttccca agtaaagttc tgtttcatat tctccttagc     60
taacttacct agttcagagt aatctgaaat agcatctact tggtcaatca aatgcgacag    120
attgccctca tctttttcc agtaacgagc tgtatcttgt gc                        162

<210> SEQ ID NO 13
<211> LENGTH: 21
<212> TYPE: DNA
<213> ORGANISM: Artificial Sequence
<220> FEATURE:
<223> OTHER INFORMATION: RGP group positive control forward primer

<400> SEQUENCE: 13
caggtgcaaa tggccaactc g                                              21

<210> SEQ ID NO 14
<211> LENGTH: 19
<212> TYPE: DNA
<213> ORGANISM: Artificial Sequence
<220> FEATURE:
<223> OTHER INFORMATION: RGP group positive control reverse primer

<400> SEQUENCE: 14
cttgccatgt tgggatgac                                                 19

<210> SEQ ID NO 15
<211> LENGTH: 30
<212> TYPE: DNA
<213> ORGANISM: Artificial Sequence
<220> FEATURE:
<223> OTHER INFORMATION: Host1

<400> SEQUENCE: 15
gaatgatact gctggcagta tttcggttgg                                     30

<210> SEQ ID NO 16
<211> LENGTH: 31
<212> TYPE: DNA
<213> ORGANISM: Artificial Sequence
<220> FEATURE:
<223> OTHER INFORMATION: Host5

<400> SEQUENCE: 16
cagtcatgta gctatcgatg aaattccaac g                                   31

<210> SEQ ID NO 17
<211> LENGTH: 801
<212> TYPE: DNA
<213> ORGANISM: Streptococcus thermophilus
```

-continued

```
<220> FEATURE:
<221> NAME/KEY: misc_feature
<223> OTHER INFORMATION: Positive control amplicon

<400> SEQUENCE: 17
caggtgcaaa tggccaactc ggaactgaac ttcgtcacct acttgatgaa cgtaacgaag      60
agtatgtagc agtagatgtg gcagaaatgg acatcacaga tgccgaaaaa gtagatgaag     120
tgtttgcgga agtaaaacca accttggttt atcactgtgc tgcttacaca gctgttgatg     180
ctgctgaaga tgaaggcaaa gagcttgact acgctattaa cgtgactggt actgaaaatg     240
tcgctaaggc tgcagaaaaa catggtgcaa cgcttgttta tatttcaacg gactacgttt     300
ttaatggtga aaaaccagtc ggtcaagagt gggaagttga tgataaacca gatccacaga     360
cagagtatgg tcgtacaaaa cgtatgggtg aagagctagt tgaaaaacat gtgactaact     420
actacattat ccgtacttcc tgggtgttcg gtaactatgg taaaaatttt gtcttcacta     480
tgcaaaacct tgctaaaact cacaagacgc tgacagtcgt taatgaccaa catggccgtc     540
caacttggac acgtactttg gcagagttta tgacttattt ggctgaaaac cgtaaggaat     600
atggttacta tcacttgtca aatgatgcaa cagaagatac aacttggtat gactttgcgg     660
ttgaaattct caaagatact gatgttgaag tgaaacctgt tgattcaagt caattcccag     720
ctaaagctaa acgtcctctt aactcaacaa tgagtttggc taaggctaag gcaacaggat     780
ttgtcatccc aacatggcaa g                                               801
```

STREPTOCOCCUS THERMOPHILUS STARTER CULTURES

CROSS-REFERENCE TO RELATED APPLICATIONS

This application is the National Stage entry of International Application No. PCT/EP2017/082776, filed 14 Dec. 2017, which claims priority to European Patent Application No. 16205245.0, filed 20 Dec. 2016.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-506000_ST25.txt" created on 17 Jun. 2019, and 6,557 bytes in size) is submitted concurrently with the instant application, and the entire contents of the Sequence Listing are incorporated herein by reference.

BACKGROUND

Field

The present invention relates to a starter culture comprising at least two *Streptococcus thermophilus* strains. Further, the present invention relates to a method for producing a starter culture. The present invention relates to a kit comprising a primer pair. The present invention relates to the use of the starter culture.

Description of Related Art

*Streptococcus thermophilus* is widely used as an acidifying and texturing bacterium in the dairy industry due its favourable technological properties (Goh et al. (2011) *Specialized adaptation of a lactic acid bacterium to the milk environment: the comparative genomics of Streptococcus thermophilus LMD-9*, Microb Cell Fact 10 Suppl 1:S22; Ott et al. (2000) *Sensory investigation of yogurt flavor perception: mutual influence of volatiles and acidity*, J Agric Food Chem 48:2, 441-50) and, thus, is of considerable value to the dairy industry worldwide. Bacterial virus (bacteriophage, or 'phage') contamination of dairy product lines severely undermines the performance of *S. thermophilus* during fermentations and may lead to a poor product or complete fermentation failure (for a review, see Quiberoni et al. (2010) *Streptococcus thermophilus bacteriophages*, International Dairy Journal 20:10, 657-64). As such, information relating to phage-host interactions in this species, as well as methods to predict and/or ameliorate fermentation spoilage by bacteriophages, is industrially useful and commercially valuable information.

The lytic bacteriophage cycle consists of a number of distinct steps. Firstly, the phage adsorbs to a receptor moiety presented on the surface of the host cell and may comprise a carbohydrate, protein or teichoic acid. This adsorption step precedes the injection of genetic material (DNA) to the interior of the cell. DNA replication is followed by assembly of viral particles and, finally, cell lysis and particle release (Sturino and Klaenhammer (2006) *Engineered bacteriophage-defence systems in bioprocessing*, Nat Rev Microbiol 4:5, 395-404). In order to successfully complete an infection cycle, bacteriophages must overcome a number of biological 'hurdles' which may be presented by the bacterial cell at certain stages in the infection process. These hurdles may include receptor masking or alteration, inhibition of DNA injection, as well as intracellular antiphage systems such as the Clustered Regularly Interspaced Short Palindromic Repeats (CRISPR) system (Barrangou et al. (2007) *CRISPR provides acquired resistance against viruses in prokaryotes*, Science 315:5819, 1709-12) or restriction/modification (R/M) systems (Guimont et al. (1993) *Restriction/modification in Streptococcus thermophilus: isolation and characterization of a type II restriction endonuclease Sth455I*, Appl Microbiol Biotechnol 39:2, 216-20). Phage-robust industrial starter strains (or blends) may consist of various derived Bacteriophage Insensitive Mutants (BIMs), which have become resistant upon exposure to phages in a laboratory setting, usually either through the CRISPR system (Mills et al. (2010) *CRISPR analysis of bacteriophage-insensitive mutants (BIMs) of industrial Streptococcus thermophilus—implications for starter design*, J Appl Microbiol 108:3, 945-55) or perhaps through a combination of mechanisms (Dupuis et al. (2013) *CRISPR-Cas and restriction-modification systems are compatible and increase phage resistance*, Nat Commun 4:2087). It is known, however, that phage circumvention of resistance systems can be rapid, with a single nucleotide polymorphism (SNP) sufficient to evade the CRISPR system (Deveau et al. (2008) *Phage response to CRISPR-encoded resistance in Streptococcus thermophilus*, J Bacteriol 190:4, 1390-400).

The phage-encoded elements responsible for the initial adsorption to cell surface receptor have been characterised, and are encoded by variable regions within the antireceptor-encoding gene (Duplessis and Moineau (2001) *Identification of a genetic determinant responsible for host specificity in Streptococcus thermophilus bacteriophages*, Mol Microbiol 41:2, 325-36). These regions are flanked by collagen-like repeats which may also indicate a certain amount of flexibility in these regions in terms of potential for DNA recombination (Duplessis et al. (2006) *Characterization of Streptococcus thermophilus host range phage mutants*, Appl Environ Microbiol 72:4, 3036-41). Due to the adaptation potential of phages in response to generated bacteriophage insensitive mutant (BIMs), it may be preferallows to attempt to 'prevent' the problem of phage infection, in combination with 'curing' through BIM generation.

Therefore, there is a need in the art for alternative approaches to increase phage robustness and to provide starter cultures with an improved phage robustness.

DESCRIPTION OF THE FIGURES

FIG. 2—Predicted open reading frame (ORF) schematic showing alignment of RGP clusters of 16 *S. thermophilus* strains (both publicly available and industrial culture collection). Arrows, representing predicted ORFs, are colour coded according to function (indicated in the legend). Amino acid identity between the protein products of adjacent ORFs is represented by shaded boxes, indicated in the legend (less than 50% identity between products is not shown). Groupings, defined using the edge clustering method (outlined in the Materials and Methods), are indicated by curved brackets as well as 'G1', 'G2', 'G3' and 'G4'. The locations of specific DNA sequences used in primer design (utilised in the multiplex RGP detection PCR; see below) are indicated by curved arrows and accompanying text, where 'P'=positive control, '1'=group 1, '2'=group 2, 3=group 3 and '4'=group 4.

SUMMARY

The present invention relates to a starter culture comprising at least two *Streptococcus thermophilus* strains, wherein a first and a second *Streptococcus thermophilus* strain are chosen from RGP group 1, RGP group 2, RGP group 3 and RGP group 4, with the proviso that the first and second *Streptococcus thermophilus* strains do not belong to the same RGP group;
  wherein RGP group 1 is defined as the group of *Streptococcus thermophilus* strains which allow to generate an amplicon by using a primer pair according to SEQ ID NO 1 and SEQ ID NO 2 in a PCR reaction;
  wherein RGP group 2 is defined as the group of *Streptococcus thermophilus* strains which allow to generate an amplicon by using a primer pair according to SEQ ID NO 4 and SEQ ID NO 5 in a PCR reaction;
  wherein RGP group 3 is defined as the group of *Streptococcus thermophilus* strains which allow to generate an amplicon by using a primer pair according to SEQ ID NO 7 and SEQ ID NO 8 in a PCR reaction;
  wherein RGP group 4 is defined as the group of *Streptococcus thermophilus* strains which allow to generate an amplicon by using a primer pair according to SEQ ID NO 10 and SEQ ID NO 11 in a PCR reaction.
Further, the present invention provides:
a starter culture of the invention, further comprising a third *Streptococcus thermophilus* strain chosen from RGP group 1, RGP group 2, RGP group 3 and RGP group 4, with the proviso that that the first, second and third *Streptococcus thermophilus* strain do not belong to the same RGP group;
a starter culture of the invention, further comprising a fourth *Streptococcus thermophilus* strain chosen from RGP group 1, RGP group 2, RGP group 3 and RGP group 4, with the proviso that that the first, second, third and fourth *Streptococcus thermophilus* strain do not belong to the same RGP group;
a starter culture of the invention, wherein the amplicon generated by using a primer pair according to SEQ ID NO 1 and SEQ ID NO 2 in a PCR reaction has a length of at least 550 bp, wherein the amplicon generated by using a primer pair according to SEQ ID NO 4 and SEQ ID NO 5 in a PCR reaction has a length of between 400 and 550 bp, wherein the amplicon generated by using a primer pair according to SEQ ID NO 7 and SEQ ID NO 8 in a PCR reaction has a length of between 250 and 350 bp and/or wherein the amplicon generated by using a primer pair according to SEQ ID NO 10 and SEQ ID NO 11 in a PCR reaction has a length of between 100 and 200 bp;
a starter culture of the invention wherein the amplicon generated by using a primer pair according to SEQ ID NO 1 and SEQ ID NO 2 in a PCR reaction has a sequence according to SEQ ID NO 3 or 90% similar thereof, wherein the amplicon generated by using a primer pair according to SEQ ID NO 4 and SEQ ID NO 5 in a PCR reaction has a sequence according to SEQ ID NO 6 or 90% similar thereof, wherein the amplicon generated by using a primer pair according to SEQ ID NO 7 and SEQ ID NO 8 in a PCR reaction has a sequence according to SEQ ID NO 9 or 90% similar thereof and/or wherein the amplicon generated by using a primer pair according to SEQ ID NO 10 and SEQ ID NO 11 in a PCR reaction has a sequence according to SEQ ID NO 12 or 90% similar thereof;
a starter culture of the invention wherein the starter culture is in a frozen or in a frieze dried form;
a method for producing a starter culture of the invention, comprising blending of *Streptococcus thermophilus* strains which do not belong to the same RGP group as defined above;
a method for producing a starter culture of the invention, further comprising a PCR to identify whether a *Streptococcus thermophilus* strain belongs to RGP group 1, RGP group 2, RGP group 3 or RGP group 4;
a method for producing a starter culture of the invention, further comprising a PCR to identify whether a *Streptococcus thermophilus* strain allows to generate an amplicon by using a primer pair according to SEQ ID NO 1 and SEQ ID NO 2, a primer pair according to SEQ ID NO 4 and SEQ ID NO 5, a primer pair according to SEQ ID NO 7 and SEQ ID NO 8 and/or a primer pair according to SEQ ID NO 10 and SEQ ID NO 11;
a method for producing a starter culture of the invention, wherein the PCR is a multiplex PCR;
a kit comprising a primer pair according to SEQ ID NO 1 and SEQ ID NO 2, a primer pair according to SEQ ID NO 4 and SEQ ID NO 5, a primer pair according to SEQ ID NO 7 and SEQ ID NO 8 and/or a primer pair according to SEQ ID NO 10 and SEQ ID NO 11;
use of the starter culture of the invention for the manufacturing of a fermented milk product;
use of the starter culture of the invention, for providing phage robustness in manufacturing of a fermented milk product.

DETAILED DESCRIPTION

The present inventors studied the rhamnose glucose polysaccharide (abbreviated as RGP) gene clusters and the link between these clusters and phage adsorption and/or infection. The present inventors identified a link between the RGP gene clusters and phage adsorption and/or infection, which link enables the grouping RGP clusters using a bioinformatic approach, leading to rapid typing of *S. thermophilus* strains into one of four defined RGP groups. Furthermore, a link between the RGP group of a given strain and its phage sensitivity profile is made, by constructing a phage-host sensitivity table of *S. thermophilus* strains whose RGP group is known, and by representative adsorption assays showing the preference of certain phages for particular RGP groups. Taken together, these findings enable a method for producing a starter culture whereby no two strains in the starter culture are of identical RGP group, providing cross-strain protection against phages which target a particular RGP group as cell surface receptor.

Therefore, the present invention relates to a starter culture comprising at least two *Streptococcus thermophilus* strains, wherein a first and a second *Streptococcus thermophilus* strain are chosen from RGP group 1, RGP group 2, RGP group 3 and RGP group 4, with the proviso that the first and second *Streptococcus thermophilus* strains do not belong to the same RGP group;

wherein RGP group 1 is defined as the group of *Streptococcus thermophilus* strains which allow to generate an amplicon by using a primer pair according to SEQ ID NO 1 and SEQ ID NO 2 in a PCR reaction;

wherein RGP group 2 is defined as the group of *Streptococcus thermophilus* strains which allow to generate an amplicon by using a primer pair according to SEQ ID NO 4 and SEQ ID NO 5 in a PCR reaction;

wherein RGP group 3 is defined as the group of *Streptococcus thermophilus* strains which allow to generate an amplicon by using a primer pair according to SEQ ID NO 7 and SEQ ID NO 8 in a PCR reaction;

wherein RGP group 4 is defined as the group of *Streptococcus thermophilus* strains which allow to generate an amplicon by using a primer pair according to SEQ ID NO 10 and SEQ ID NO 11 in a PCR reaction.

By blending *Streptococcus thermophilus* strains from different RGP groups into a starter culture, the phage robustness of the starter culture is increased because the phages have a preference for a single RGP group. Therefore, in a preferred embodiment, the present starter culture has an improved phage robustness in comparison with starter cultures comprising *Streptococcus thermophilus* strains of the same RGP group. In another preferred embodiment, the present starter culture does not comprise *Streptococcus thermophilus* strains belonging to the same RGP group.

The term "starter culture" as used herein refers to a culture of one or more food-grade micro-organisms, in particular lactic acid bacteria, which are responsible for the acidification of the milk base. Starter cultures may be fresh (liquid), frozen or freeze-dried. Freeze dried cultures need to be regenerated before use. For the production of a fermented dairy product, the starter is usually added in an amount from 0.01 to 3%, preferably from 0.01 and 0.02% by weight of the total amount of milk base.

The term PCR reaction as used in the present context has its normal meaning of the art, and the skilled person knows general PCR conditions for the successful generation of amplicons. An example of reaction conditions is as follows: initial denaturation of 95° C. for 10 minutes, 30 cycles of 95° C. for 15 seconds, 55° C. for 30 sec and 72° C. for 1 min, with a final extension of 72° C. for 10 min. Other reactions conditions allowing the PCR reactions are also envisaged.

The term 'primer pair according to SEQ ID NO x and SEQ ID NO y' as used in the present context means a primer pair comprising a primer according to SEQ ID NO x and a primer according to SEQ ID NO y.

The term at least two *Streptococcus thermophilus* strains' means that the present starter cultures may comprise more than two *Streptococcus thermophilus* strains. For example a third, a fourth, or a fifth *Streptococcus thermophilus* strain.

Preferably the present starter culture comprises a *Lactobacillus delbrueckii* subsp. *Bulgaricus* strain. A starter culture comprising both *Streptococcus thermophilus* strains and a *Lactobacillus delbrueckii* subsp. *Bulgaricus* strain is suitable for the manufacturing of yogurt.

The term 'allow generate an amplicon' as used in the present context refers to the ability to produce one or more copies of a part of the DNA of the respective strain. An alternative for the term amplicon is PCR product.

Alternatively, RGP group 1 can be defined as the group of *Streptococcus thermophilus* strains comprising a nucleotide sequence according to SEQ ID NO 3 or at least 80%, 85% or at least 90% similar thereof, such as at least 91%, 92%, 93%, 94%, 95%, 96%, 97%, 98%, or at least 99%;

RGP group 2 can be defined as the group of *Streptococcus thermophilus* strains comprising a nucleotide sequence according to SEQ ID NO 6 or at least 80%, 85% or at least 90% similar thereof such as at least 91%, 92%, 93%, 94%, 95%, 96%, 97%, 98%, or at least 99%;

RGP group 3 can be defined as the group of *Streptococcus thermophilus* strains comprising a nucleotide sequence according to SEQ ID NO 9, or at least 80%, 85% or at least 90% similar thereof such as at least 91%, 92%, 93%, 94%, 95%, 96%, 97%, 98%, or at least 99%; and/or RGP group 4 can be defined as the group of *Streptococcus thermophilus* strains comprising a nucleotide sequence according to SEQ ID NO 12, or at least 80%, 85% or at least 90% similar thereof such as at least 91%, 92%, 93%, 94%, 95%, 96%, 97%, 98%, or at least 99%.

The term 'do not belong to the same RGP group' as used herein means that the *Streptococcus thermophilus* strains belong to different RGP groups. For example, the present starter may comprise a *Streptococcus thermophilus* strain belonging to RGP group 1 and a *Streptococcus thermophilus* strain belonging to RGP group 2, 3 or 4. Preferably, the present *Streptococcus thermophilus* strains do not belong to the same RGP group chosen from RGP group 1, 2, 3 and 4 as defined herein.

In a preferred embodiment, the present starter cultures further comprises a third or a fourth *Streptococcus thermophilus* strain chosen from RGP group 1, RGP group 2, RGP group 3 and RGP group 4, with the proviso that that the first, second and third or that the first, second, third and fourth *Streptococcus thermophilus* strain do not belong to the same RGP group. By inclusion of *Streptococcus thermophilus* strain chosen from different RGP groups the starter culture becomes more phage robust, for example against several different phages. In the event that phages are present which might infect *Streptococcus thermophilus* strains belonging to for example RGP group 1 and 2, the inclusion of a *Streptococcus thermophilus* strain chosen from RGP group 3 and/or 4 provides phage robustness because the *Streptococcus thermophilus* strain chosen from RGP group 3 and/or 4 are not infected by the phages which might infect *Streptococcus thermophilus* strains belonging to for example RGP group 1 and 2.

In a preferred embodiment, the present amplicon generated by using a primer pair according to SEQ ID NO 1 and SEQ ID NO 2 in a PCR reaction has a length of at least 550 bp, wherein the amplicon generated by using a primer pair according to SEQ ID NO 4 and SEQ ID NO 5 in a PCR reaction has a length of between 400 and 550 bp, wherein the amplicon generated by using a primer pair according to SEQ ID NO 7 and SEQ ID NO 8 in a PCR reaction has a length of between 250 and 350 bp and/or wherein the amplicon generated by using a primer pair according to SEQ ID NO 10 and SEQ ID NO 11 in a PCR reaction has a length of between 100 and 200 bp. The advantage of the present amplicons is that their difference in length is sufficient for a visual analysis. An example which allows a visual analysis is in an electrophoretic examination using a 1% agarose gel, on which the amplicons were separated at 100 V for at least 20 minutes.

More preferably the present amplicon generated by using a primer pair according to SEQ ID NO 1 and SEQ ID NO 2 in a PCR reaction has a length of between 600 and 650 bp, more preferably a length between 625 and 635 bp, such as 631 bp.

More preferably the present amplicon generated by using a primer pair according to SEQ ID NO 4 and SEQ ID NO 5 in a PCR reaction has a length of between 440 and 490 bp, more preferably a length between 460 and 470 bp, such as 464 bp.

More preferably the present amplicon generated by using a primer pair according to SEQ ID NO 7 and SEQ ID NO 8 in a PCR reaction has a length of between 275 and 325 bp, more preferably a length between 300 and 310 bp, such as 303 bp.

More preferably the present amplicon generated by using a primer pair according to SEQ ID NO 10 and SEQ ID NO 11 in a PCR reaction has a length of between 140 and 190 bp, more preferably a length between 160 and 170 bp, such as 164 bp.

In a preferred embodiment, the present amplicon generated by using a primer pair according to SEQ ID NO 1 and SEQ ID NO 2 in a PCR reaction has a sequence according to SEQ ID NO 3 or at least 90% similar thereof, such as at least 91%, 92%, 93%, 94%, 95%, 96%, 97%, 98%, or at least 99%;

the amplicon generated by using a primer pair according to SEQ ID NO 4 and SEQ ID NO 5 in a PCR reaction has a sequence according to SEQ ID NO 6 or at least 90% similar thereof, such as at least 91%, 92%, 93%, 94%, 95%, 96%, 97%, 98%, or at least 99%;

the amplicon generated by using a primer pair according to SEQ ID NO 7 and SEQ ID NO 8 in a PCR reaction has a sequence according to SEQ ID NO 9 or at least 90% similar thereof, such as at least 91%, 92%, 93%, 94%, 95%, 96%, 97%, 98%, or at least 99%; and/or the amplicon generated by using a primer pair according to SEQ ID NO 10 and SEQ ID NO 11 in a PCR reaction has a sequence according to SEQ ID NO 12 or at least 90% similar thereof such as at least 91%, 92%, 93%, 94%, 95%, 96%, 97%, 98%, or at least 99%.

The terms "sequence similarity" or "sequence homology" are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleotides/bases or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labelled in the output of the program as "longest-identity".

In a preferred embodiment, the present starter culture is in a frozen or in a frieze dried form. More preferably the present starter culture is packaged in a package suitable for commercial use. More preferably the present starter culture is packaged in a package of at least 50 gram frozen or frieze dried starter culture, more preferably at least 500 gram frozen or frieze dried starter culture, most preferably at least 5 kilogram frozen or frieze dried starter culture. It is advantageous to package the present starter culture in a package, which is suitable for a commercial use because the dairy industry suffers from phage infection and thus could benefit from the starter culture of the present invention.

In a preferred embodiment, the present invention relates to a method for producing a starter culture, comprising a step to identify whether a *Streptococcus thermophilus* strain belongs to RGP group 1, RGP group 2, RGP group 3 or RGP group 4, as defined herein. The present step can be a sequence homology (search). For example, a sequence homology (search) to identify the presence of an amplicon according to SEQ ID NO 3, SEQ ID NO 6, SEQ ID NO 9 or SEQ ID NO 12 or at least 90% similar thereof, such as at least 91%, 92%, 93%, 94%, 95%, 96%, 97%, 98%, or at least 99%. More preferably, the present step is a PCR.

Preferably, the present PCR, or PCR reaction, is conducted in a total volume of 25 µl using Taq polymerase, according to manufacturer's instructions (Qiagen, Hilden, Germany). An example of reaction conditions is as follows: initial denaturation of 95° C. for 10 minutes, 30 cycles of 95° C. for 15 seconds, 55° C. for 30 sec and 72° C. for 1 min, with a final extension of 72° C. for 10 min.

More preferably the present method further comprises blending of *Streptococcus thermophilus* strains which do not belong to the same RGP group as defined herein. Preferably the present invention relates to a method for producing the starter culture of the invention, comprising blending of *Streptococcus thermophilus* strains which do not belong to the same RGP group as defined herein. More preferably the present method comprises blending at least two *Streptococcus thermophilus* strains, wherein a first and a second *Streptococcus thermophilus* strain are chosen from RGP group 1, RGP group 2, RGP group 3 and RGP group 4, with the proviso that the first and second *Streptococcus thermophilus* strains do not belong to the same RGP group. More preferably, the present method comprises blending a third or a fourth *Streptococcus thermophilus* strain chosen from RGP group 1. RGP group 2, RGP group 3 and RGP group 4, with the proviso that that the first, second and third or that the first, second, third and fourth *Streptococcus thermophilus* strain do not belong to the same RGP group.

Preferably, the present method further comprises a PCR to identify whether a *Streptococcus thermophilus* strain allows to generate an amplicon by using a primer pair according to SEQ ID NO 1 and SEQ ID NO 2, a primer pair according to SEQ ID NO 4 and SEQ ID NO 5, a primer pair according to SEQ ID NO 7 and SEQ ID NO 8 and/or a primer pair according to SEQ ID NO 10 and SEQ ID NO 11.

Preferably, the present method further comprises a PCR to identify whether a *Streptococcus thermophilus* strain allows to generate an amplicon according to SEQ ID NO 3, SEQ ID NO 6, SEQ ID NO 9 or SEQ ID NO 12 or at least 90% similar thereof, such as at least 91%, 92%, 93%, 94%, 95%, 96%, 97%, 98%, or at least 99%.

In a more preferred embodiment, the present PCR is a multiplex PCR. More preferably a multiplex PCR comprising the primer pair according to SEQ ID NO 1 and SEQ ID NO 2, the primer pair according to SEQ ID NO 4 and SEQ ID NO 5, the primer pair according to SEQ ID NO 7 and SEQ ID NO 8 and the primer pair according to SEQ ID NO 10 and SEQ ID NO 11. The advantage of using a multiplex PCR is that the present amplicons of varying size which are specific for the RGP groups can be produced. This allows an efficient process to identify the RGP groups of a group of *Streptococcus thermophilus* strains, for example in developing a rotation scheme. A rotation scheme can be efficiently produced by identifying the RGP groups of *Streptococcus thermophilus* strains in starter culture suffering from phage infection, and then combine the starter culture with a *Streptococcus thermophilus* strain from another RGP group.

Therefore, in a preferred embodiment, the present invention relates to a kit comprising a primer pair according to SEQ ID NO 1 and SEQ ID NO 2, a primer pair according to SEQ ID NO 4 and SEQ ID NO 5, a primer pair according to SEQ ID NO 7 and SEQ ID NO 8 and/or a primer pair according to SEQ ID NO 10 and SEQ ID NO 11.

Further, the present invention relates to the use of a starter culture of the invention, for the manufacturing of a fermented milk product. More preferably, the present invention relates to the use of a starter culture of the present invention, for providing phage robustness in manufacturing of a fermented milk product. The present invention also relates to the use of the present starter culture for providing a rotation scheme against phage infection.

As used in this specification, the term "fermented dairy product" or "acidified dairy product" is intended to refer to products which are obtained by the multiplication of lactic acid bacteria in a milk base leading to a milk coagulum. The milk preparation used as raw material for the fermentation may be skimmed or non-skimmed milk, optionally concentrated or in the form of powder. Furthermore, this milk preparation may have been subjected to a thermal processing operation which is at least as efficient as pasteurization. The particular characteristics of the various fermented dairy products depend upon various factors, such as the composition of milk base, the incubation temperature, the lactic acid flora and/or non-lactic acid flora. Thus, fermented dairy products manufactured herein include, for instance, various types of regular yoghurt, low fat yoghurt, non fat yoghurt, kefir, dahi, ymer, buttermilk, butterfat, sour cream and sour whipped cream as well as fresh cheeses such as quark and cottage cheese.

As used in the present specification, the term "yoghurt" refers to products comprising "lactic acid bacteria such as *Streptococcus salivarius thermophilus* and *Lactobacillus delbruekii* subsp. *bulgaricus*, but also, optionally, other microorganisms such as *Lactobacillus delbruekii* subsp. *lactis*, *Bifidobacterium animalis* subsp. *lactis*, *Lactococcus lactis*, *Lactobacillus acidophilus* and *Lactobacillus casei*, or any microorganism derived therefrom. The lactic acid strains other than *Streptococcus salivarius thermophilus* and *Lactobacillus delbruekii* subsp. *bulgaricus*, are intended to give the finished product various properties, such as the property of promoting the equilibrium of the flora.

The invention is further illustrated in the example below.

Materials and Methods

1. Bacterial Storage and Growth Conditions

The bacterial strains and phages applied in the present invention are listed in Table 1.

*Streptococcus thermophilus* strains were routinely grown from single colonies, from 20% reconstituted skimmed milk (RSM) stocks or from 10% glycerol stocks overnight at 42° C. in M17 broth (Oxoid, Hampshire, U.K.) supplemented with 0.5% lactose (LM17; Sigma-Aldrich, St. Louis, Mo., U.S.A.).

TABLE 1

Bacterial strains and phages applied in the present invention

| Isolate | RGP Group | Source |
|---|---|---|
| Bacterial strains | | |
| ST13 | 1 | DSM, The Netherlands |
| ST4576 | 1 | " |
| ST4577 | 1 | " |
| ST800 | 1 | " |
| ST665 | 2 | " |
| 300-F | 2 | " |
| 100-F | 4 | " |
| NGB48.1 | 4 | " |
| ST3 | 2 | " |
| ST820 | 1 | " |
| ST110 | 4 | " |
| ST14 | 2 | " |
| 200-E | 4 | " |
| ST802 | 3 | " |
| ST144 | 3 | " |
| UCCST4 | 1 | UCC, Cork, Ireland |

TABLE 1-continued

Bacterial strains and phages applied in the present invention

| Isolate | RGP Group | Source |
| --- | --- | --- |
| UCCST5 | 1 | " |
| UCCST6 | 4 | " |
| UCCST7 | 2 | " |
| UCCST11 | 1 | " |
| UCCT1 | 4 | " |
| Bacteriophages | | |
| ST13D1A-L | | DSM, The Netherlands |
| ST13D2A-L | | " |
| ST13D4A-L | | " |
| ST4576D1A-L | | " |
| ST4576D2A-L | | " |
| ST4577D1A-L | | " |
| ST4577D3A-L | | " |
| ST665D2A-S | | " |
| ST800D1B-L | | " |
| NGBD1A-L | | " |
| ST802D1B-E | | " |
| ST144 D1A-M | | " |
| 300FD2A-L | | " |
| ST110 D1A-L | | " |
| ST4A3 | | UCC, Cork, Ireland |
| ST5B1 | | " |
| ST6B2 | | " |
| ST7B3 | | " |
| ST11F | | " |
| W1A | | " |
| W3B | | " |
| W3A | | " |
| W7D | | " |
| T1A | | " |

2. Bacteriophage Isolation, Propagation, Enumeration and Storage

Whey samples sourced from dairy processing plants were analysed for the presence of phages using spot assay and plaque assay tests (Lillehaug (1997) *An improved plaque assay for poor plaque-producing temperate lactococcal bacteriophages*, J Appl Microbiol 83:1, 85-90), whereby LM17 broth (as above) was supplemented with 0.25% glycine and either 10 g/L (solid agar base) or 4 g/L (semi-solid overlay) technical agar (VWR Chemicals, Radnor, Pa., U.S.A.). Single plaques were propagated (at least twice to ensure pure phage preparations) according to the method of Moineau et al. ((1994) Evolution of a Lytic Bacteriophage via DNA Acquisition from the *Lactococcus lactis* Chromosome, Appl Environ Microbiol 60:6, 1832-41). Resultant lysates were filtered (0.45 μm; Sarstedt, Nümbrecht, Germany) and stored at 4° C. for use in subsequent assays.

3. Phage-Host Analysis

The host ranges of twenty-two individual phage isolates were determined using a bank of twenty-one strains of *S. thermophilus* (listed in Table 1) by employing the spot assay method as above. Briefly, 400 μl fresh overnight culture was added to 4 ml semi-solid agar and vortexed briefly. The mixture was plated on solid agar (as above) and allowed to dry before 10 μl undiluted phage lysate was placed on the plate. The plate was then allowed to dry before incubation under microaerophilic conditions at 42° C. overnight. Where a zone of lysis was observed, this was indicated in the phage-host table as '+', while no symbol (blank) indicated no visible lysis or plaques. Hazy or single plaques (considered to be a low level phage infection) are indicated by a '1' mark.

4. In Silico Analysis and Multiplex PCR RGP Typing

Figure 1:
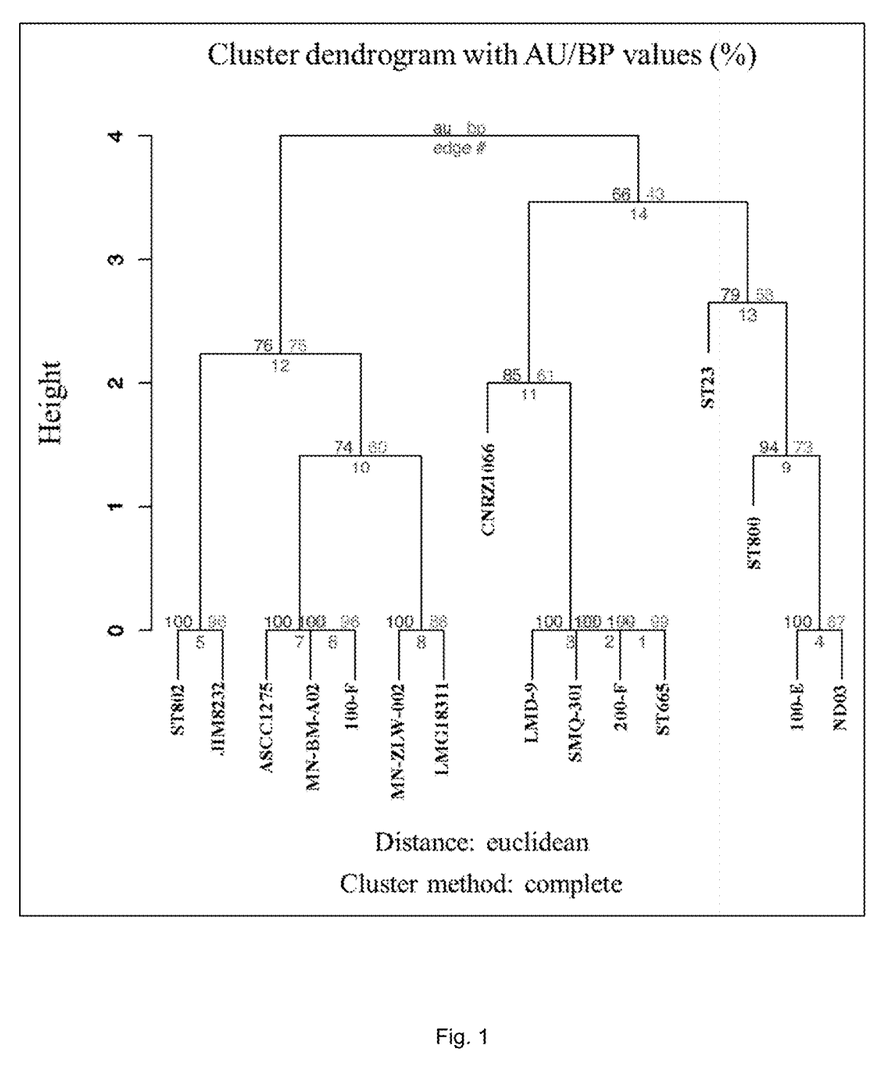
FIG. 1—Dendrogram showing the genetic distance between the RGP gene clusters of sixteen *S. thermophilus* strains. Using the present data set, an edge clustering value (expressed as Euclidean distance) of 11 or greater was used to define distinct groups of RGP clusters. The significance of this clustering method is indicated by accompanying p-values (of at least 60; left of branches) and bootstrap values (of at least 40; right of branches), which were generated as described in the Materials and Methods.

In silico analysis of the complete genomes of both published and DSM collection *S. thermophilus* strains allowed the definition of RGP clusters based on their (i) genetic content, being composed of several genes involved in carbohydrate polymer production (such as glycosyl/rhamnosyl-transferases), (ii) position in the respective genomes and (iii) flanking genes, being functionally conserved at either end of the clusters despite the inherent variability of the clusters. Deduced amino acid sequences of predicted RGP cluster ORFS were first compared using all-vs-all BLAST (Altschul et al., Mol Biol 1990) alignment, followed by Markov (MCL) clustering (Van Dongen (2001) Graph clustering by flow simulation) with the aim of grouping all the genes in functional related families sharing at least 50% of similarity over 50% of protein length (cut-off e-value of 0.0001). Presence/absence of all gene families across strains was used to divide members into distinct RGP groups by means of the statistical R package pvuclust cran.r-project.org/web/packages/pvclust/index.html), which calculates, for each group, the probability value for the node or cluster to occur over a random resampling of 1000 replicates. The cluster analysis also returns the minimum finite value (expressed as Euclidean distance between points) used to create each node of the hierarchical tree (called edge clustering value), which we used to define groups or subgroups, based on the occurrence of all the gene families across strains (FIG. 1). Using the present data set, an edge clustering value of 11 or greater was used to define distinct groups of rgp clusters.

A visual assessment of the gene content and organization of such clusters was also performed and compared to the cluster analysis, (FIG. 2) including the information on sequence identity between genes retrieved using BLASTP alignments (Altschul et al. (1990) *Basic local alignment search tool*, J Mol Biol 215:3, 403-10). Following RGP group assignment, the PCR primer pairs listed in Table 2 were designed on nucleotide sequences that are unique to each RGP group (the specific targets of the primers are indicted using numbers in FIG. 2), and colony PCRs performed on each strain. Each PCR reaction contained all primer sets listed in Table 2 (with the exception of HOST1 and HOST5), i.e. the positive control pair and four pairs representing each RGP group. PCR reactions, which used a portion of fresh bacterial colony as template, were conducted in a total volume of 25 μl using Taq polymerase, according to manufacturer's instructions (Qiagen, Hilden, Germany). Reaction conditions were as follows: initial denaturation of 95° C. for 10 minutes, 30 cycles of 95° C. for 15 seconds, 55° C. for 30 sec and 72° C. for 1 min, with a final extension of 72° C. for 10 min.

TABLE 2

PCR primers applied in the present invention

| SEQ ID NO | Primer name | Sequence (5'-3') | Target | Product size (bp) | source |
| --- | --- | --- | --- | --- | --- |
| 13 | RGPposF | CAGGTGCAAATGGCCAACTCG | All RGP groups | | UCC, Cork, Ireland |

TABLE 2-continued

PCR primers applied in the present invention

| SEQ ID NO | Primer name | Sequence (5'-3') | Target | Product size (bp) | source |
|---|---|---|---|---|---|
| 14 | RGPposR | CTTGCCATGTTGGGATGAC | " | 801 | " |
| 1 | RGPgroup1F | GGATGATGGTTCGACGGATAG | RGP group 1 | | " |
| 2 | RGPgroup1R | CCGCTCTTCCAAAACCATGA | " | 631 | " |
| 4 | RGPgroup2F | GTGAAGAGTCAGAAGACGAAT | RGP group 2 | | " |
| 5 | RGPgroup2R | CAAAGGCCCCGATGGTATT | " | 464 | " |
| 7 | RGPgroup3F | GAGGAAGCAACAGATAAACGA | RGP group 3 | | " |
| 8 | RGPgroup3R | GACCAATTGGTCCACAAAAGT | " | 303 | " |
| 10 | RGPgroup4F | CTCCTCGTACTCACCCAC | RGP group 4 | | " |
| 11 | RGPgroup4R | GCACAAGATACAGCTCGTTAC | " | 162 | " |
| 15 | HOST1 | GAATGATACTGCTGGCAGTATTTCGGTTGG | Phage VR2 region | | Binetti et al., 2005 |
| 16 | HOST5 | CAGTCATGTAGCTATCGATGAAATTCCAACG | " | | " |

TABLE 3

Amplicon sequences

| SEQ ID NO | Amplicon name | Sequence |
|---|---|---|
| 3 | RGP group 1 | ggatgatggttcgacggatagttcaactcaaattatccaagaggttttgaaggattcacctttttgagacaagatttgaaactcatgaaaacctggggtagtaaagaatcgaaatttaggattagagcttataagaggtgactatttgctatttgtagatagtgataactacctcgatgcggattatgtggaacagttgtacagtaagttgacggaaacaaatgctgatattgcgtactgtgatctttttaatccagaaaaagaagagttctaccttaaaagccgtgaatttgacctaactgcctttctaaatgctagttttattgataactgttctttgattcgtagaagtattattggaaatgctcgttatgatgagatgtttaaatcgtaaaaagcttgaagattatgacttttttattgaacttaatcattaataacggtgctaaagcggtatatcaaccaagcactaagcttaattatcgtgtctttgaaacaggatcaatttctggacgtgactccgttcgctaccattatgaaatctatcttgacattcttgagaagtaccttgataagcttcctcatgaaatttacaaggcagtttgtgagaacctcatggttttggaagagcgg |
| 6 | RGP group 2 | gtgaagagtcagaagacgaataattgatttgttttatattcatagcaatggcgacttgaacagtcgcttttcttttgtattaggaaaaaagcccagaaaatggtataattgagtggattgtaatttgtaagaaaggaaataatatgcaacacgttttattatcggaagtcgtggactttccggctcaatatggtggtttcgagaccttcgtggaccaattggtctccaatcgagtatcaccgaatatcaagtaccatgttgcttgcctttctaatgatcaagcctactatcatttgactacaagggtgtagattgttttacgattaaagcacccaaacttgggcctgcgcgggtcattgcctatgatatgatggccatcaattatgccttgaaggtcattaagaaacaaggaattgaaaaacctatttttttatattttgggcaataccatcggggcctttg |
| 9 | RGP group 3 | gaggaagcaacagataaacgagaatattttgtttatgttattgccaatctatttatattgatgtcagtagtattgacaatccttcagtactatggtgtgaaaaataattttttaactttttcaagtagtcctttgtggctgcttttctgtttgcaataggcaaaatctttgtaaaatggtataattgactagattatagacttgttagaaagggggatttatgcaacaacacgtattcattattggaagtcgtgggcttccgtctcaatatgcgcggttttgagactttttgtgaccaattggtc |
| 12 | RGP group 4 | ctcctcgtactcacccacaattttttcccaagtaaagttctgtttcatattctccttagctaacttacctagttcagagtaatctgaaatagcatctacttggtcaatcaaatgcgacagattgccctcatctttttttccagtaacgagctgtatcttgtgc |
| 17 | Positive control | caggtgcaaatggccaactcggaactgaacttcgtcacctacttgatgaacgtaacgaagagtatgtagcagtagatgtggcagaaatggacatcacagatgccgaaaaagtagatgaagtgtttgcggaagtaaaaccaaccttggtttatcactgtgctgcttacacagctgttgatgctgctgaagatgaaggcaaagagcttgactacgctattaacgtgactggtactgaaaatgtcgctaaggctgcagaaaaaacatggtgcaacgcttgtttatattttcaacggactacgttt |

TABLE 3-continued

Amplicon sequences

| SEQ ID NO | Amplicon name | Sequence |
|---|---|---|
| | | ttaatggtgaaaaaccagtcggtcaagagtgggaagttgatgataaaccagatccacaga cagagtatggtcgtacaaaacgtatgggtgaagagctagttgaaaaacatgtgactaact actacattatccgtacttcctgggtgttcggtaactatggtaaaaattttgtottcacta tgcaaaaccttgctaaaactcacaagacgctgacagtcgttaatgaccaacatggccgtc caacttggacacgtactttggcagagtttatgacttatttggctgaaaaccgtaaggaat atggttactatcacttgtcaaatgatgcaacagaagatacaacttggtatgactttgcgg ttgaaattctcaaagatactgatgttgaagtgaaacctgttgattcaagtcaattcccag ctaaagctaaacgtcctcttaactcaacaatgagtttggctaaggctaaggcaacaggat ttgtcatcccaacatggcaag |

15

5. Adsorption Assays

Determination of phage adsorption to selected bacterial strains was determined using a method adapted from (Garvey et al. (1996) *The Lactococcal Plasmid pNP40 Encodes a Third Bacteriophage Resistance Mechanism, One Which Affects Phage DNA Penetration*, Appl Environ Microbiol 62:2, 676-9). Briefly, 10 ml of pre-warmed LM17 broth was inoculated (2%) from a fresh overnight culture of the appropriate strain. Growth was allowed to proceed at 42° C. until the $OD_{600nm}$ was within the range of 0.5 and 0.54. 700 µl of the growing culture was transferred to a 1.5 ml microcentrifuge tube and centrifuged at 5000×g for 10 minutes to pellet the cells. The supernatant was removed and the cells were resuspended in 700 µl of ¼ strength Ringers solution (Merck, Darmstadt, Germany). An equal volume of the appropriate phage lysate (diluted to an approximate titer of $10^5$ pfu/ml) was added to the tube or to 700 µl buffer (negative control). The mixture was incubated at 42° C. for 12 mins and centrifuged at 15,000×g for 3 minutes to remove bacterial cells before 150 µl of the residual phage-containing supernatant was removed for enumeration by plaque assay as described above. Calculation of adsorption levels (as a percentage of total number of phages present) was performed as follows: ([Control phage titre−Free phage titre in supernatant]/Control phage titre)×100.

6. Phage VR2 Region Analysis

Variable region 2 (VR2) regions were isolated by one of two methods. PCR amplification of VR2 regions were performed using the HOST primer pair described listed in Table 2 and as previously described by (Binetti et al. (2005) *Detection and characterization of Streptococcus thermophilus bacteriophages by use of the antireceptor gene sequence*, Appl Environ Microbiol 71:10, 6096-103). Resultant PCR products were purified using a JetQuick PCR purification spin kit (Genomed, Lohne, Germany) and sequenced by Sanger sequencing (MWG Biotech, Ebersberg, Germany). Sequences were subsequently assembled using the Seqman program (DNAStar, Madison, Wash., U.S.A.).

VR2 regions were also extracted from complete phage genome sequences. In order to determine these genome sequences, individual phages were propagated as described above in a 2 L volume before the addition of (poly)ethylene glycol (Sigma Aldrich, St. Louis, Mo., U.S.A.) to a final volume of 10% (w/v) and NaCl (Sigma Aldrich, St. Louis, Mo., U.S.A.) to a final concentration of 0.5 M. The mixtures were incubated at 4° C. for at least six hours before centrifugation at 17,700×g for 15 mins and resuspension in 5 ml TBT Buffer (100 mM NaCl, 100 mM Tris-HCl (pH 7), 10 mM $MgCl_2$, 20 mM $CaCl_2$; Sigma Aldrich, St. Louis, Mo., U.S.A.). The suspension was extracted at least twice using an equal volume of chloroform (Fisher Scientific, Waltham, Mass., U.S.A.) and phages were purified by a discontinuous (3 M/5 M) cesium chloride (Sigma Aldrich) gradient centrifugation at 76,000×g for 2.5 hours. Translucent blue bands visible at the interface of the gradient after centrifugation were carefully removed using a syringe and dialysed against 50 ml TBT overnight at 4° C. Phage preparations were stored at 4° C. until DNA extraction. Phage DNA was prepared using a method adapted from (Moineau, Pandian (1994) *Evolution of a Lytic Bacteriophage via DNA Acquisition from the Lactococcus lactis Chromosome*, Appl Environ IVIicrobiol 60:6, 1832-41). Briefly, 20 µl proteinase K (20 mg/ml; Fisher Scientific) was added to 200 µl CsCl purified phage and the mixture placed at 56° C. for 20 mins. Sodium dodecyl sulphate solution (SDS; Sigma Aldrich) was added to a final concentration of 1-1.5% before heating at 65° C. for 30 mins. Potassium acetate was added to a final concentration of 1 M and the mixture placed on ice for 30 mins. Centrifugation at 13,200×g was followed by phenol chloroform:isoamyl alcohol (25:24:1; Sigma Aldrich) extraction and the addition of 0.1 volume of 3 M sodium acetate and 2.5 volumes of ice cold 96% ethanol (Sigma Aldrich). Precipitated phage DNA was pelleted at 21,000×g and resuspended in 50 µl TE buffer (10 mM Tris-HCl, 1 mM EDTA, pH 7.5). At least 5 µg DNA was extracted using this method and quantified using a NanoDrop 2000 (Thermo Scientific, Waltham, Mass., U.S.A.). Total genomic DNA was qualitatively analysed by electrophoretic examination using a 1% agarose (Sigma-Aldrich) gel, on which the samples were separated at 100 V for at least 20 minutes. Phage genomes were sequenced by random shotgun sequencing using pyrosequencing technology by Macrogen, Inc. (Geumcheon-gu, Seoul, South Korea) using a 454 FLX instrument yielding at least 85 fold coverage for each genome. Individual sequence files were assembled using GSassembler (454 Lifesciences, Branford, Conn., U.S.A.), generating a consensus sequences for each phage. VR2 regions were extracted based on alignment of the sequences of the antireceptor-encoding genes with those of the HOST1 and HOST5 primers listed in Table 2. VR2 regions were aligned and the genetic relatedness tree visualised using MUSCLE multiple alignment by the MEGA program (Tamura et al. (2007) MEGA4: Molecular Evolutionary Genetics Analysis (MEGA) software version 4.0, Mol Biol Evol 24:8, 1596-9).

EXAMPLE

Linkage of Bacterial RGP Group and Phage Infection and/or Adsorption Profile

1. Construction of Phage-Host Table

Figure 4:
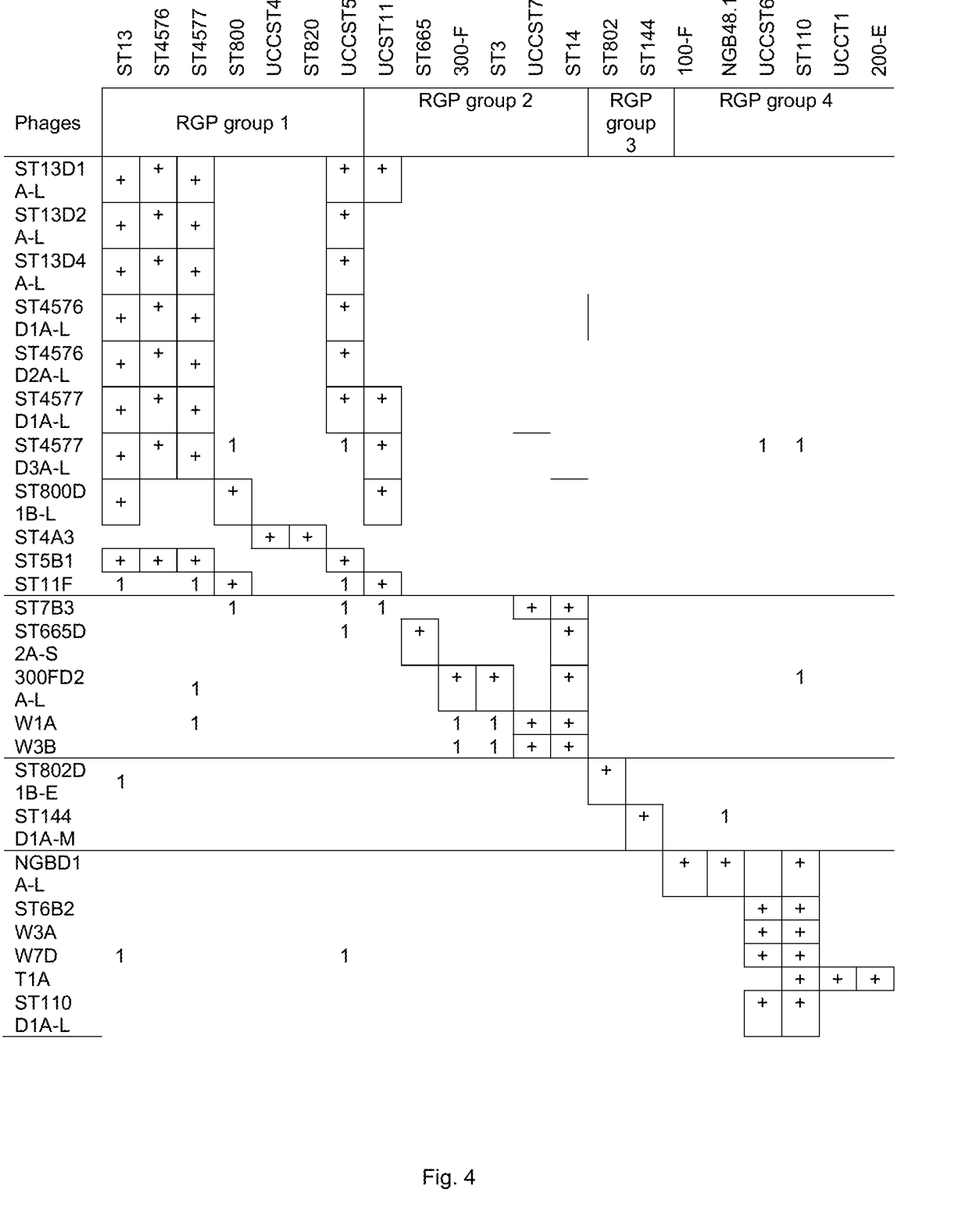
FIG. 4. Host range analysis of bacteriophages and bacterial strains applied in the present invention. '+' indicates a clear zone of lysis was observed upon spot assay test. '1' indicates that single or hazy plaques were observed in the same test, and these interactions are classified as 'non-host' interactions for the purposes of the adsorption analysis (FIG. 5).

The phages listed in Table 1 were assayed for infection against each *S. thermophilus* strain using the spot assay method outlined above, the results of which are shown in FIG. 4. Bacterial strains were chosen at random from a larger collection of industrial starter cultures based on their being susceptible to at least two phage isolates—exceptions being ST802 and ST144 which are infected by one phage isolate each, but which have been included in this study as a representative of RGP group 3. Construction of the ph age-host table was made without prior knowledge of RGP group.

2. Multiplex PCR RGP Group Typing of Bacterial Strains

Figure 2:
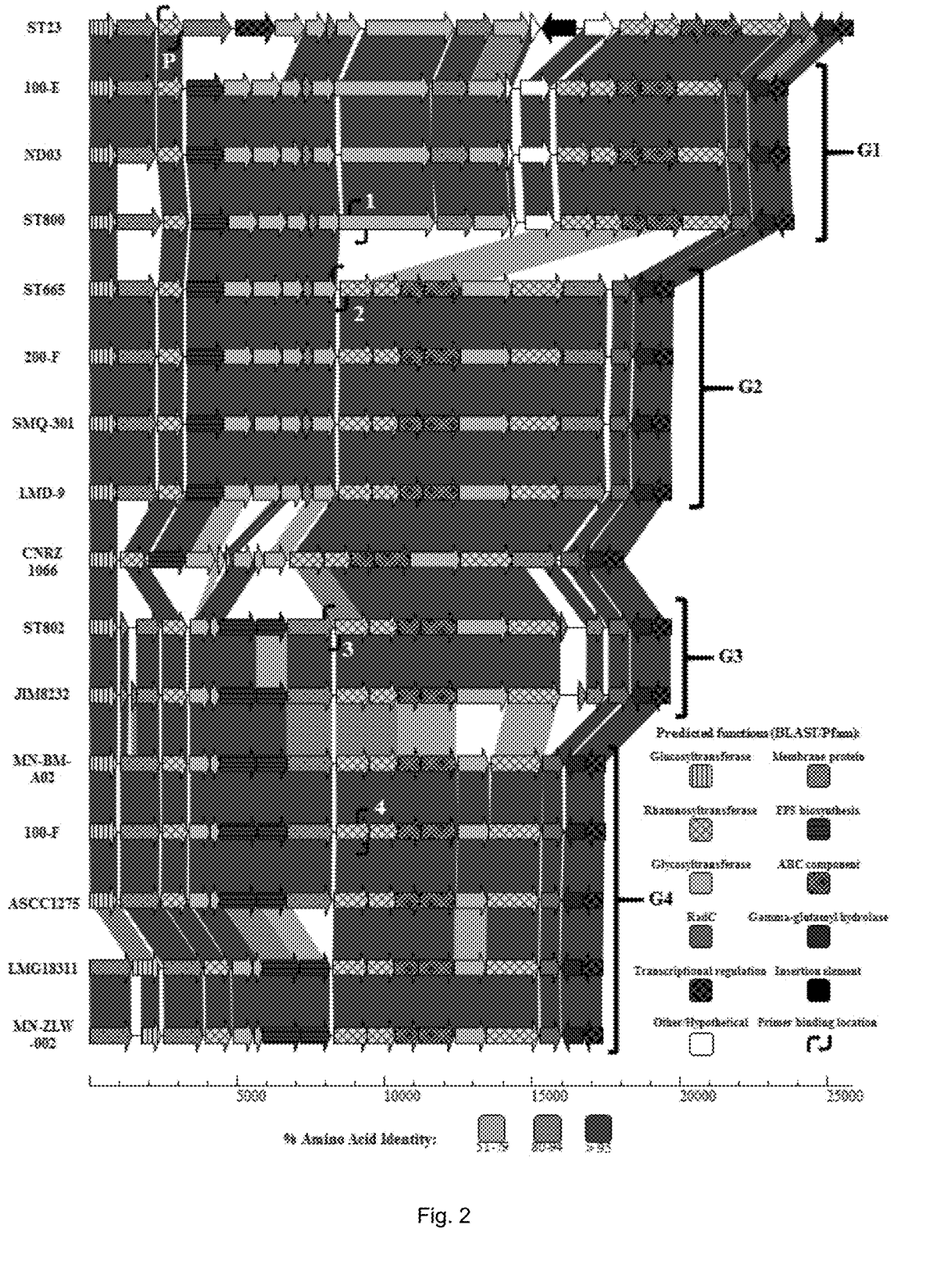

The RGP gene clusters of nine publicly available *S. thermophilus* bacterial genomes (ncbi.nlm.nih.gov), as well as seven strains from the DSM culture collection (of which four were applied in the phage host analysis described above), were extracted from whole genome sequences and grouped as described in the MATERIALS AND METHODS, the results of which are shown in FIGS. 1 and 2. A dendrogram showing the genetic distance between each strain is shown I FIG. 1. In FIG. 2, deduced amino acid sequences of predicted ORFS showing greater than 50% identity are connected by shaded boxes. The deduced RGP groupings, of which there are four (excepting two outliers, namely ST23 and CNRZ1066), are indicated by curved brackets in FIG. 2.

Figure 3:
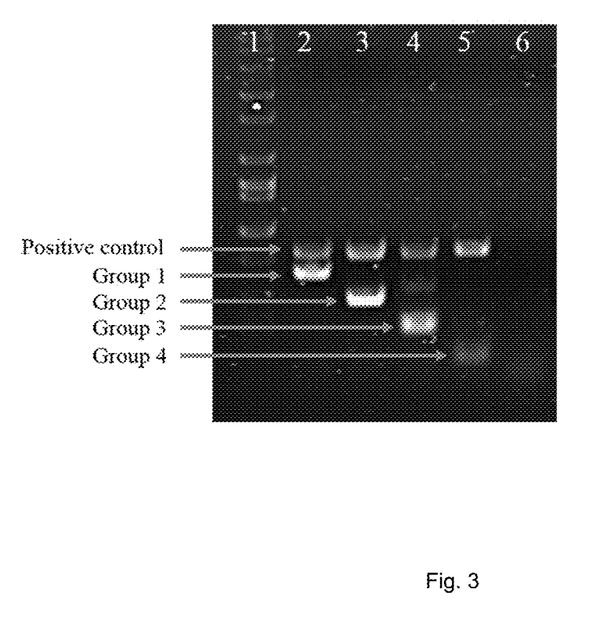
FIG. 3—PCR amplification of RGP-group defining elements of representative *S. thermophilus* strains applied in the present invention. Lanes 1: 1 kb Full Scale DNA Ladder (Fisher Scientific, U.S.A.), L2: ST800 (RGP Group 1 control), L3: ST665 (RGP Group 2 control), L4: ST802 (RGP Group 3 control), L5: 100F (RGP group 4 control), L6: Negative control. The primers used in this amplification are described in Table 2.

Based on these deduced RGP groupings (FIG. 1; and as outlined in the MATERIALS AND METHODS), five sets of PCR primers were designed to enable the rapid detection of these four groups. PCR primer targets are approximately indicated by curved arrows in FIG. 2, and include a 'positive control' set (indicated by 'P') which was designed on a predicted rhamnosyltransferase-encoding gene, found to be highly conserved in the rgp clusters of all strains analysed. Representative example results of the PCR typing analysis is shown in FIG. 3. A PCR product showing a size of approximately 800 basepairs (bp), consistent with the predicted size of the positive control PCR product, was amplified from each strain analysed. No product was amplified from the negative control sample (FIG. 3, Lane 6). Four *S. thermophilus* strains from the DSM culture collection, containing nucleotide sequences upon which the applied primer sets had been designed, were included in this analysis as positive controls for each RGP group (FIG. 3, Lanes 2-5). Each strain analysed by this method could be grouped into one of the four deduced RGP groupings.

3. Link Between RGP Groupings and Phage Infectivity

Following the results of the RGP typing PCR (above), bacterial strains applied in the phage-host survey were grouped by RGP group in order to visualise the relationship between phage infectivity and the possession of a particular type of rgp gene cluster. The results of this analysis are shown in FIG. 4, which show a clear preference of all phages for strains expressing one of the four deduced RGP groups. Of 24 phages analysed, all were shown to infect (with the exception of low level infection) only strains expressing either Group 1, 2, 3 or 4. In all cases, where the primary host for the phages were of a particular RGP group, the secondary, and (where applicable) tertiary, quaternary and quinary hosts for the phage were also of that group.

4. Link Between RGP Groupings and Phage Adsorption

Adsorption assays using representative phages ST4577D1A-L, UCCST7B3, ST144D1A-M and ST110 DIA-L were performed using (i) the primary host of the phage, (ii) a host (panel A, RGP group 1) or non-host (panels B, C and D) of the same RGP group as the primary host, and (iii) six non-host strains expressing RGP groups that are distinct from its primary host, as described in the MATERIAL AND METHODS. The results of this analysis are shown in FIG. 5.

Figure 5:
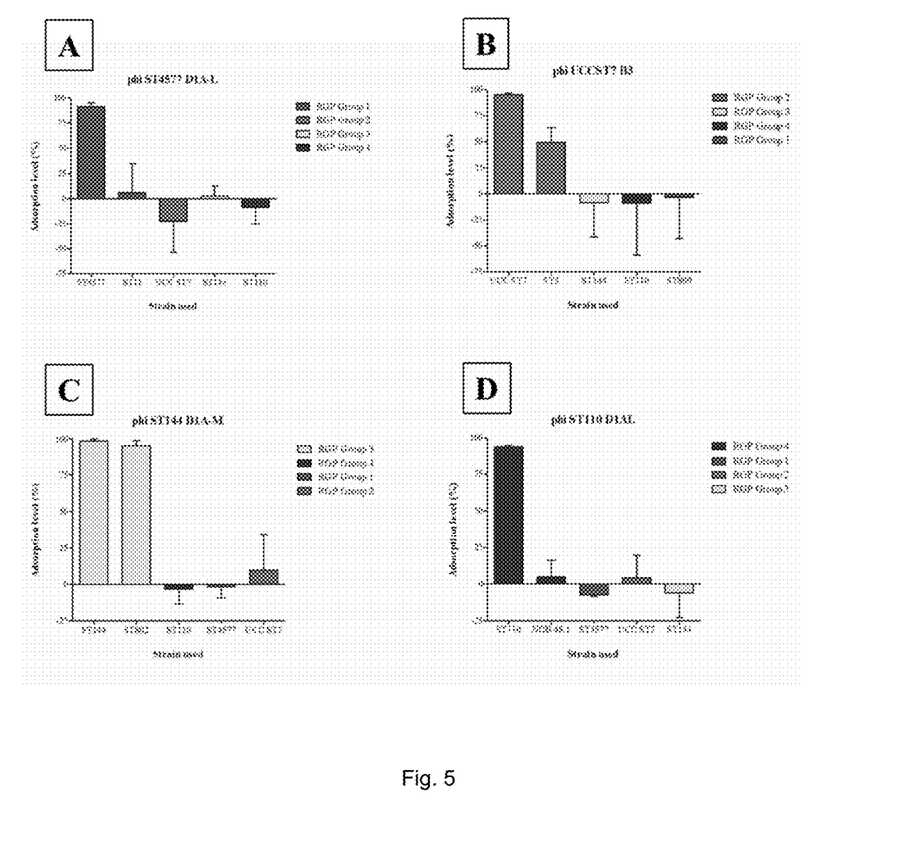
FIG. 5—Adsorption level of phages ST4577 D1A-L (Panel 'A'; infecting RGP group 1 strain ST4577), UCCST7B3 ('B'; infecting RGP group 2 strain UCC ST7), ST144 D1A-M ('C'; infecting RGP group 3 strain ST144) and ST110D1A-L (D'; infecting RGP group 4 strain ST110) on (i) their primary host (first column), (ii) a host (panel A) or non-host (panels B, C and D) strain of the same RGP group as the primary host (second column), (iii) three non-host strains of differing RGP groups (third, fourth and fifth columns).

From the results shown in FIG. 5 it is clear that the phages used in this analysis have a highly specific preference for particular RGP groups—being either 1, 2, 3 or 4. In the cases of RGP groups 2 and 3 strains, this is borne out by the observation that phages whose primary host expresses a particular RGP group, a secondary strain also expressing this group has the ability to adsorb this phage to a high level despite not being an infective host (FIG. 5). As mentioned above, infection of these strains may be stopped at a 'downstream' stage of infection, i.e. phage DNA injection or intracellular replication. Significantly, strains expressing a distinct RGP group to the primary host of a particular phage could not, in any case, adsorb that same phage to a high level. This indicates that strains expressing distinct RGP groups to the primary host of the phage may present another 'hurdle' to the phage, whereas strains expressing the same group do not present this hurdle and, therefore, are inherently more susceptible to similar phages. Exceptions to this general trend can be expected, potentially due to (i) as-yet-unknown factors relating to the interaction of the phage RBP and cell surface receptor at the molecular level, or (ii) the possible existence of RGP subtypes which may present distinct polysaccharide structures on the bacterial cell surface mentioned above. Nonetheless, the examples outlined above indicate that RGP typing provides an indication as to the adsorption preference of certain phages.

---

The invention claimed is:

1. A starter culture comprising at least a first *Streptococcus thermophilus* strain and a second *Streptococcus thermophilus* strain, wherein:
the first and second *Streptococcus thermophilus* strains are chosen from the groups consisting of rhamnose glucose polysaccharide (RGP) group 1, RGP group 2, RGP group 3, and RGP group 4, with the proviso that the first and second *Streptococcus thermophilus* strains do not belong to the same RGP group;
and wherein:
RGP group 1 is defined as the group of *Streptococcus thermophilus* strains which allow generation of an amplicon by using a primer pair having nucleotide sequences SEQ ID NO:1 and SEQ ID NO:2 in a PCR reaction;
RGP group 2 is defined as the group of *Streptococcus thermophilus* strains which allow generation of an amplicon by using a primer pair having nucleotide sequences SEQ ID NO:4 and SEQ ID NO:5 in a PCR reaction;
RGP group 3 is defined as the group of *Streptococcus thermophilus* strains which allow generation of an amplicon by using a primer pair having nucleotide sequences SEQ ID NO:7 and SEQ ID NO:8 in a PCR reaction; and
RGP group 4 is defined as the group of *Streptococcus thermophilus* strains which allow to generation of an amplicon by using a primer pair having nucleotide sequences SEQ ID NO:10 and SEQ ID NO:11 in a PCR reaction.

2. The starter culture of claim 1, further comprising a third *Streptococcus thermophilus* strain chosen from RGP group 1, RGP group 2, RGP group 3 and RGP group 4, with the proviso that the first, second, and third *Streptococcus thermophilus* strains do not belong to the same RGP group.

3. The starter culture of claim 1, further comprising a fourth *Streptococcus thermophilus* strain chosen from RGP group 1, RGP group 2, RGP group 3 and RGP group 4, with the proviso that the first, second, third, and fourth *Streptococcus thermophilus* strains do not belong to the same RGP group.

4. The starter culture of claim 1, wherein:
the amplicon generated by using a primer pair having nucleotide sequences SEQ ID NO:1 and SEQ ID NO:2 in a PCR reaction has a length of at least 550 bp;
the amplicon generated by using a primer pair having nucleotide sequences SEQ ID NO:4 and SEQ ID NO:5 in a PCR reaction has a length of between 400 and 550 bp;
the amplicon generated by using a primer pair having nucleotide sequences SEQ ID NO:7 and SEQ ID NO:8 in a PCR reaction has a length of between 250 and 350 bp; and/or
the amplicon generated by using a primer pair having nucleotide sequences SEQ ID NO:10 and SEQ ID NO:11 in a PCR reaction has a length of between 100 and 200 bp.

5. The starter culture according to of claim 1, wherein:
the amplicon generated by using a primer pair having nucleotide sequences SEQ ID NO:1 and SEQ ID NO:2 in a PCR reaction has the nucleotide sequence of SEQ ID NO:3 or at least 90% similarity thereto;
the amplicon generated by using a primer pair having nucleotide sequences SEQ ID NO:4 and SEQ ID NO:5 in a PCR reaction has the nucleotide sequence of SEQ ID NO:6 or at least 90% similarity thereto;
the amplicon generated by using a primer pair having nucleotide sequences SEQ ID NO:7 and SEQ ID NO:8 in a PCR reaction has the nucleotide sequence of SEQ ID NO:9 or at least 90% similarity thereto; and/or the amplicon generated by using a primer pair having nucleotide sequences SEQ ID NO:10 and SEQ ID NO:11 in a PCR reaction has the nucleotide sequence of SEQ ID NO:12 or at least 90% similarity thereto.

6. The starter culture of claim 1, wherein the starter culture is in a frozen or in a freeze-dried form.

7. A method for producing a starter culture, comprising identifying whether a *Streptococcus thermophilus* strain belongs to rhamnose glucose polysaccharide (RGP) group 1, RGP group 2, RGP group 3, or RGP group 4 and blending at least two of said *Streptococcus thermophilus* strains which do not belong to the same RGP groups, wherein:

RGP group 1 is defined as the group of *Streptococcus thermophilus* strains which allow generation of an amplicon by using a primer pair having nucleotide sequences SEQ ID NO:1 and SEQ ID NO:2 in a PCR reaction;

RGP group 2 is defined as the group of *Streptococcus thermophilus* strains which allow generation of an amplicon by using a primer pair having nucleotide sequences SEQ ID NO:4 and SEQ ID NO:5 in a PCR reaction;

RGP group 3 is defined as the group of *Streptococcus thermophilus* strains which allow generation of an amplicon by using a primer pair having nucleotide sequences SEQ ID NO:7 and SEQ ID NO:8 in a PCR reaction; and RGP group 4 is defined as the group of *Streptococcus thermophilus* strains which allow generation of an amplicon by using a primer pair having nucleotide sequences SEQ ID NO:10 and SEQ ID NO:11 in a PCR reaction.

8. The method for producing a starter culture of claim 7, wherein the identifying whether a *Streptococcus thermophilus* strain belongs to RGP group 1, RGP group 2, RGP group 3, or RGP group 4 is performed by a sequence homology or a PCR.

9. The method for producing a starter culture of claim 7, further comprising performing a PCR to identify whether a *Streptococcus thermophilus* strain allows generation of an amplicon by using a primer pair having: nucleotide sequences SEQ ID NO:1 and SEQ ID NO:2; a primer pair having nucleotide sequences SEQ ID NO:4 and SEQ ID NO:5; a primer pair having nucleotide sequences SEQ ID NO:7 and SEQ ID NO:8; and/or a primer pair having nucleotide sequences SEQ ID NO:10 and SEQ ID NO:11.

10. The method for producing a starter culture of claim 8, wherein the PCR is a multiplex PCR.

11. A product comprising the starter culture of claim 1, for manufacturing of a fermented milk product.

12. A product comprising the starter culture of claim 1, for providing phage robustness in manufacturing of a fermented milk product.

* * * * *